US009867799B2

(12) United States Patent
Saccone et al.

(10) Patent No.: US 9,867,799 B2
(45) Date of Patent: *Jan. 16, 2018

(54) DIETHYL-[6-(4-HYDROXYCARBAMOYL-PHENYL-CARBAMOYLOXY-METHYL)-NAPHTHALEN-2-YL-METHYL]-AMMONIUM CHLORIDE FOR USE IN THE TREATMENT OF MUSCULAR DYSTROPHY

(71) Applicant: ITALFARMACO S.P.A., Milan (IT)

(72) Inventors: Valentina Saccone, Naples (IT); Silvia Consalvi, Ciampino (IT); Pier Lorenzo Puri, Rome (IT); Paolo Mascagni, Villasanta (IT)

(73) Assignee: ITALFARMACO S.P.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/208,957

(22) Filed: Jul. 13, 2016

(65) Prior Publication Data

US 2016/0346243 A1 Dec. 1, 2016

Related U.S. Application Data

(63) Continuation of application No. 14/444,959, filed on Jul. 28, 2014, now Pat. No. 9,421,184, which is a continuation of application No. PCT/IT2012/000040, filed on Feb. 3, 2012.

(51) Int. Cl.
*A61K 31/27* (2006.01)
*A61K 31/167* (2006.01)
*A61K 31/325* (2006.01)
*A61K 31/573* (2006.01)
*A61K 45/06* (2006.01)
*A61K 31/58* (2006.01)
*A61K 9/00* (2006.01)

(52) U.S. Cl.
CPC ............ *A61K 31/27* (2013.01); *A61K 9/0095* (2013.01); *A61K 31/167* (2013.01); *A61K 31/325* (2013.01); *A61K 31/573* (2013.01); *A61K 31/58* (2013.01); *A61K 45/06* (2013.01)

(58) Field of Classification Search
None
See application file for complete search history.

(56) References Cited

U.S. PATENT DOCUMENTS

| 5,538,721 A * | 7/1996 | Babcock | A61K 9/0048 424/450 |
|---|---|---|---|
| 7,229,963 B2 | 6/2007 | Sartorelli et al. | |
| 7,795,208 B2 | 9/2010 | Sartorelli et al. | |
| 2008/0160108 A1 | 7/2008 | De La Porte et al. | |
| 2009/0149430 A1 | 6/2009 | Pignol et al. | |
| 2011/0021494 A1 * | 1/2011 | Maier | C07D 471/04 514/210.21 |
| 2011/0237663 A1 * | 9/2011 | Mascagni | A61K 31/17 514/479 |

FOREIGN PATENT DOCUMENTS

| FR | 2 847 817 | 6/2004 |
|---|---|---|
| FR | 2 898 274 | 9/2007 |
| WO | WO 2003/013493 | 2/2003 |
| WO | WO 2004/065355 | 8/2004 |
| WO | WO 2008/101121 | 8/2008 |
| WO | WO 2011/048514 | 4/2011 |
| WO | WO 2011 /092556 | 8/2011 |

OTHER PUBLICATIONS

Colussi, et al.; "Histone Deacetylase Inhibitors: Keeping Momentum for Neuromuscular and Cardiovascular Diseases Treatment"; Pharmacological Research; vol. 62, No. 1, pp. 3-10 (Jul. 2010).
Colussi, et al.; "The Histone Deacetylase Inhibitor Suberoylanilide Hydroxamic Acid Reduces Cardiac Arrhythmias in Dystrophic Mice"; Cardiovascular Research; vol. 87, No. 1, pp. 73-82 (Jul. 2010).
Consalvi, et al.; "Histone Deacetylase Inhibitors in the Treatment of Muscular Dystrophies: Epigenetic Drugs for Genetic Diseases"; Molecular Medicine; vol. 17, No. 5-6, pp. 457-465 (May 2011 ).
Dinarello, et al.; "Histone Deacetylase Inhibitors for Treating a Spectrum of Diseases Not Related to Cancer"; Molecular Medicine; vol. 17, No. 5-6, pp. 333-352 (May 2011 ).
Grounds, et al.; "Towards Developing Standard Operating Procedures for Pre-Clinical Testing in the MDX Mouse Model of Duchenne Muscular Dystrophy"; Neurobiology of Disease; vol. 31, pp. 1-19 (2008).
International Search Report and Written Opinion of International Application No. PCT/IT2012/000040 dated Jun. 12, 2012.
Komaki, Hirofumi, "Corticosteroids Therapy for Duchenne Muscular Dystrophy", Myopathy, 2009, pp. 29-32 with English Abstract.
"The Merck Manual", (18th edition, Japanese version), p. 2606-2608, Published on Apr. 25, 2007 by Nikkei Bushiness Publications, Inc., Supervised by Masanori Fukushima, Sold by Nikkei Bushiness Publications Center (1-17-3, Shirogane, Minato-ku, Tokyo 108-8646).

(Continued)

*Primary Examiner* — David J Blanchard
*Assistant Examiner* — Sarah Chickos
(74) *Attorney, Agent, or Firm* — Perkins Coie LLP; Viola T. Kung

(57) ABSTRACT

The present invention relates to a method for treating muscular dystrophy which comprises administering diethyl-[6-(4-hydroxycarbamoyl-phenyl-carbamoyloxy-methyl)-naphthalen-2-yl-methyl]-ammonium chloride or other pharmaceutically acceptable salts and/or solvates thereof to a patient in need of such a treatment. The invention further relates to a method for treating muscular dystrophy which comprises administering diethyl-[6-(4-hydroxycarbamoyl-phenyl-carbamoyloxy-methyl)-naphthalen-2-yl-methyl]-ammonium chloride or other pharmaceutically acceptable salts and/or solvates thereof in combination with one or more additional anti-inflammatory active agents to a patient in need of such a treatment.

16 Claims, 3 Drawing Sheets

(56) References Cited

OTHER PUBLICATIONS

Minetti, et al.; "Functional and Morphological Recovery of Dystrophic Muscles in Mice Treated with Deacetylase Inhibitors"; Nature Medicine; vol. 12, No. 10, pps. 1147-1150 (Oct. 2006).

* cited by examiner

DIETHYL-[6-(4-HYDROXYCARBAMOYL-PHENYL-CARBAMOYLOXY-METHYL)-NAPHTHALEN-2-YL-METHYL]-AMMONIUM CHLORIDE FOR USE IN THE TREATMENT OF MUSCULAR DYSTROPHY

This application is a continuation of U.S. patent application Ser. No. 14/444,959, filed Jul. 28, 2014; which is a continuation of PCT/IT2012/000040, filed Feb. 3, 2012; the contents of the above-identified applications are incorporated herein by reference in their entirety.

TECHNICAL FIELD

The present invention relates to a method for treating muscular dystrophy which comprises administering diethyl-[6-(4-hydroxycarbamoyl-phenyl-carbamoyloxy-methyl)-naphthalen-2-yl-methyl]-ammonium chloride or other pharmaceutically acceptable salts and/or solvates thereof to a patient in need of such a treatment.

The invention further relates to a method for treating muscular dystrophy which comprises administering diethyl-[6-(4-hydroxycarbamoyl-phenyl-carbamoyloxy-methyl)-naphthalen-2-yl-methyl]-ammonium chloride or other pharmaceutically acceptable salts and/or solvates thereof in combination with one or more additional anti-inflammatory active agents to a patient in need of such a treatment.

BACKGROUND OF THE INVENTION

Muscular dystrophies (MDs) include a heterogeneous group of genetic diseases invariably leading to muscle degeneration and impaired function. Mutation of nearly 30 genes gives rise to various forms of muscular dystrophy, which differ in age of onset, severity, and muscle groups affected (Dalkilic I, Kunkel L M. (2003) Muscular dystrophies: genes to pathogenesis. Curr. Opin. Genet. Dev. 13:231-238).

The most common MD is the Duchenne muscular dystrophy (DMD), a severe recessive X-linked disease which affects one in 3,500 males, characterized by rapid progression of muscle degeneration, eventually leading to loss of ambulation and death within the second decade of life.

Attempts to replace or correct the mutated gene, by means of gene or cell therapy, might result in a definitive solution for muscular dystrophy, but this is not easy to achieve. Alternative strategies that prevent or delay muscle degeneration, reduce inflammation or promote muscle metabolism or regeneration might all benefit patients and, in the future, synergize with gene or cell therapy. Steroids that reduce inflammation are currently the only therapeutic tool used in the majority of DMD patients (Cossu G, Sampaolesi M. (2007) New therapies for Duchenne muscular dystrophy: challenges, prospects and clinical trials. TRENDS Mol. Med. 13:520-526). Diethyl-[6-(4-hydroxycarbamoyl-phenyl-carbamoyloxy-methyl)-naphthalen-2-yl-methyl]-ammonium chloride, which is described in WO 97/43251 (anhydrous form) and in WO 2004/065355 (monohydrate crystal form), herein both incorporated by reference, is an anti-inflammatory agent which is able to inhibit the synthesis of the majority of pro-inflammatory cytokines whilst sparing anti-inflammatory ones.

Diethyl-[6-(4-hydroxycarbamoyl-phenyl-carbamoyloxy-methyl)-naphthalen-2-yl-methyl]-ammonium chloride is also known as ITF2357.

The monohydrate crystal form of diethyl-[6-(4-hydroxycarbamoyl-phenyl-carbamoyloxy-methyl)-naphthalen-2-yl-methyl]-ammonium chloride is known as Givinostat.

Givinostat is being evaluated in several clinical studies, including studies for the treatment of myeloproliferative diseases, polycythemia vera, periodic fever syndrome, Crohn's disease and systemic-onset juvenile idiopathic arthritis. Orphan drug designation was assigned in the E.U. for the treatment of systemic-onset juvenile idiopathic arthritis and for the treatment of polycythemia vera.

Givinostat has been recently found to act also as a Histone Deacetylase inhibitor (WO 2011/048514).

Histone deacetylases (HDAC) are a family of enzymes capable of removing the acetyl group bound to the lysine residues in the N-terminal portion of histones or in other proteins. HDACs can be subdivided into four classes, on the basis of structural homologies. Class I HDACs (HDAC 1, 2, 3 and 8) are similar to the RPD3 yeast protein and are located in the cell nucleus. Class II HDACs (HDAC 4, 5, 6, 7, 9 and 10) are similar to the HDA1 yeast protein and are located both in the nucleus and in the cytoplasm. Class III HDACs are a structurally distinct form of NAD-dependent enzymes correlated with the SIR2 yeast protein. Class IV (HDAC 11) consists at the moment of a single enzyme having particular structural characteristics. The HDACs of classes I, II and IV are zinc enzymes and can be inhibited by various classes of molecule: hydroxamic acid derivatives, cyclic tetrapeptides, short-chain fatty acids, aminobenzamides, derivatives of electrophilic ketones, and the like. Class III HDACs are not inhibited by hydroxamic acids, and their inhibitors have structural characteristics different from those of the other classes.

The expression "histone deacetylase inhibitor" in relation to the present invention is to be understood as meaning any molecule of natural, recombinant or synthetic origin capable of inhibiting the activity of at least one of the enzymes classified as histone deacetylases of class I, class II or class IV.

Although HDAC inhibitors, as a class, are considered to be potentially useful as anti-tumor agents, it is worth to note that, till now, only two of them (Vorinostat and Romidepsin) have been approved as drugs for the cure of a single tumor form (Cutaneous T-cell lymphoma).

It is evident that the pharmaceutical properties of each HDAC inhibitor may be different and depend on the specific profile of inhibitory potency, relative to the diverse isoenzymes as well as on the particular pharmacokinetic behaviour and tissue distribution.

Some HDAC inhibitors have been claimed to be potentially useful, in combination with other agents, for the treatment of DMD (WO 2003/033678, WO 2004/050076, Consalvi S. et al. Histone Deacetylase Inhibitors in the Treatment of Muscular Dystrophies: Epigenetic Drugs for Genetic Diseases. (2011) Mol. Med. 17:457-465).

The potential therapeutic use of HDAC inhibitors in DMD may however be hampered by the possible harmful effects of these relatively toxic agents, especially when used for long-term therapies in paediatric patients.

Givinostat, as anti-inflammatory agent, has been already used in a phase II study in children with Systemic Onset Juvenile Idiopathic Arthritis; Givinostat administered at 1.5 mg/kg/day for twelve weeks achieved ACR Pedi 30, 50 and 70 improvement of approximately 70% (Vojinovic J, Nemanja D. (2011) HDAC Inhibition in Rheumatoid Arthritis and Juvenile Idiopathic Arthritis. Mol. Med 17:397-403) showing only a limited number of mild or moderate but short lasting, adverse effects.

To date more than 500 patients (including 29 children) have been treated with Givinostat. Repeated dose toxicity studies were carried out in dogs, rats and monkeys. Oral daily doses of the drug were administered up to nine consecutive months. The drug was well tolerated with no overt toxicity at high doses. The "no adverse effect levels" (NOAEL) ranged from 10 to 25 mg/kg/day depending on the animal species and the duration of treatment.

In juvenile animals Givinostat at 60 mg/kg/day did not affect the behavioural and physical development and reproductive performance of pups.

No genotoxic effect was detected for Givinostat in the mouse lymphoma assay and the chromosomal aberration assay in vitro and in the micronucleus test and UDS test in vivo.

DETAILED DESCRIPTION OF THE INVENTION

Figure 1:
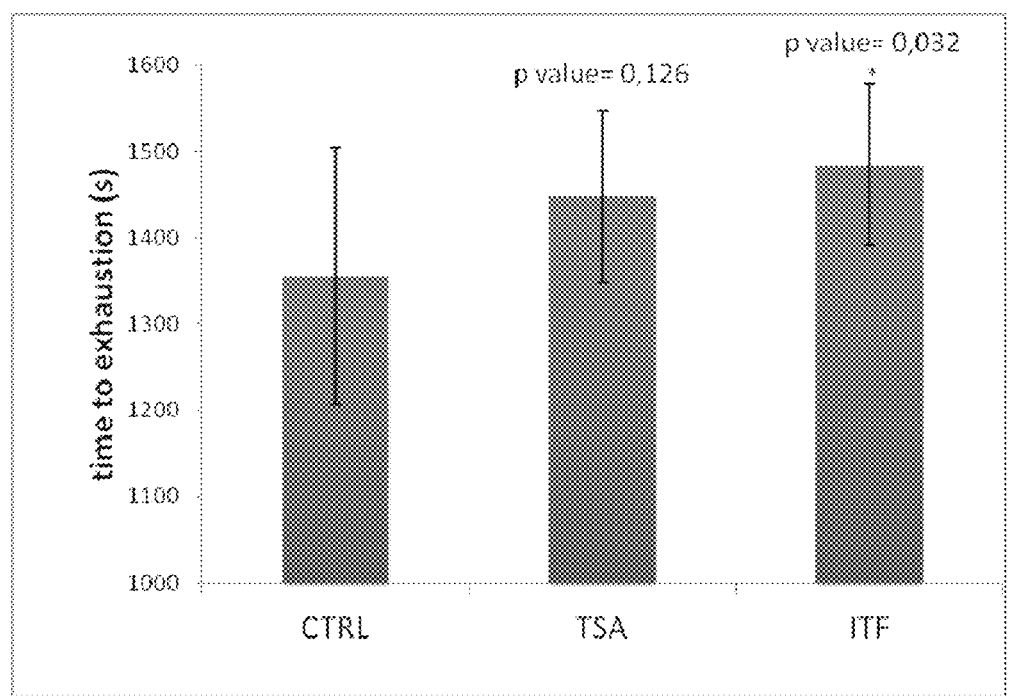
FIG. 1 shows time to exhaustion in control group, TSA-treated group, and ITF-treated group.

We have now found that the administration of diethyl-[6-(4-hydroxycarbamoyl-phenyl-carbamoyloxy-methyl)-naphthalen-2-yl-methyl]-ammonium chloride is able to prevent or delay muscle degeneration, reduce inflammation and promote muscle metabolism or regeneration.

An object of the present invention is therefore a method for treating muscular dystrophy, which comprises administering diethyl-[6-(4-hydroxycarbamoyl-phenylcarbamoyloxymethyl)-naphthalen-2-yl-methyl]-ammonium chloride, preferably in monohydrate form, more preferably in monohydrate crystal form, or other pharmaceutically acceptable salts and/or solvates thereof, to a patient in need of such treatment.

The muscular dystrophy is, preferably, the Duchenne muscular dystrophy.

Diethyl-[6-(4-hydroxycarbamoyl-phenylcarbamoyloxymethyl)-naphthalen-2-yl-methyl]-ammonium chloride, preferably in monohydrate form, more preferably in monohydrate crystal form, or other pharmaceutically acceptable salts and/or solvates thereof of the invention is administered in an amount ranging from 0.5 to 15 mg/kg/day, preferably from 1 to 10 mg/kg/day. More preferably, it is administered on a daily basis.

For the purpose of the present invention diethyl-[6-(4-hydroxycarbamoyl-phenylcarbamoyloxymethyl)-naphthalen-2-yl methyl]-ammonium chloride (or other pharmaceutically acceptable salts and/or solvates thereof) is administered in the form of a pharmaceutical composition containing the same together with at least one physiologically acceptable excipient.

Said pharmaceutical composition is preferably administered to the patient by enteral and/or parenteral route, preferably by oral, sublingual, rectal, intravascular, intravenous, subcutaneous route, more preferably by oral route.

The pharmaceutical composition can be formulated in a solid or a liquid form. Preferably, said solid form is selected from tablet, granulate, aggregate, compressed or coated pill, hard or gelatine capsule and said liquid form is selected from suspension or syrup.

The pharmaceutical composition of the invention preferably contains from 7.5 to 200 mg of diethyl-[6-(4-hydroxycarbamoyl-phenylcarbamoyloxymethyl)-naphthalen-2-yl-methyl]-ammonium chloride or other pharmaceutically acceptable salts and/or solvates thereof, more preferably from 25 to 150 mg, per unit dosage form.

For the purposes of the present invention, diethyl-[6-(4-hydroxycarbamoyl-phenylcarbamoyloxymethyl)-naphthalen-2-yl-methyl]-ammonium chloride or other pharmaceutically acceptable salts and/or solvates thereof can be effectively administered alone or it can be administered in combination with at least one additional anti-inflammatory active agent.

According to a preferred embodiment of the invention, said "at least one additional anti-inflammatory active agent" is a steroid.

The steroid is preferably a glucocorticoid corticosteroid, more preferably it is selected from the group consisting of prednisolone, prednisone, deflazacort, hydrocortisone, methylprednisolone, dexamethasone, betamethasone, triamcinolone, beclometasone, fludrocortisone acetate, deoxycorticosterone acetate, even more preferably it is selected from prednisolone and deflazacort.

The combination therapy according to the present invention includes administration of a single pharmaceutical dosage formulation comprising diethyl-[6-(4-hydroxycarbamoyl-phenylcarbamoyloxymethyl)-naphthalen-2-yl methyl]-ammonium chloride or other pharmaceutically acceptable salts and/or solvates thereof and the at least one additional anti-inflammatory active agent, as well as the administration of diethyl-[6-(4-hydroxycarbamoyl-phenylcarbamoyloxymethyl)-naphthalen-2-yl methyl]-ammonium chloride or other pharmaceutically acceptable salts and/or solvates thereof and the at least one additional anti-inflammatory active agent each in their own separate pharmaceutical dosage formulations.

When a single dosage formulation is used, it may contain from 7.5 to 200 mg of diethyl-[6-(4-hydroxycarbamoyl-phenylcarbamoyloxymethyl)-naphthalen-2-yl-methyl]-ammonium chloride or the pharmaceutically acceptable salts and/or solvates thereof, preferably from 25 to 150, and from 0.25 to 2.5 mg/kg of said at least one anti-inflammatory active agent, preferably from 0.5 to 1 mg/kg.

Where separate dosage formulations are used, diethyl-[6-(4-hydroxycarbamoyl-phenylcarbamoyloxymethyl)-naphthalen-2-yl methyl]-ammonium chloride or other pharmaceutically acceptable salts and/or solvates thereof and the at least one additional active agent can be administered at essentially the same time, i.e., concurrently; or at separately staggered times, i.e., sequentially. The combination therapy according to the present invention is understood to include all these regimens.

According to one embodiment of the present invention, the recipient of the claimed method is a child.

In more detail, diethyl-[6-(4-hydroxycarbamoyl-phenylcarbamoyloxymethyl)-naphthalen-2-yl-methyl]-ammonium chloride or other pharmaceutically acceptable salts and/or solvates thereof, either alone or in combination with at least one additional active agent or the pharmaceutical composition thereof is administered to a child, preferably on a daily basis, in an amount ranging from 0.5 to 15 mg/kg/day, preferably from 1.0 to 10 mg/kg/day.

The following examples are intended to be illustrative of the invention rather than limiting the scope thereof.

EXAMPLES

Introduction

The animal model chosen for the experiment was the C57BL/10ScSn-Dmdmdx/J mouse (hereafter "mdx"). The mdx mouse, an X-linked myopathic mutant, is the most amenable and approachable disease model for preclinical studies on human Duchenne muscular dystrophy. The mdx mouse has a single base substitution within an exon, which causes premature termination of the polypeptide chain. This mutation is X chromosome-linked and produces viable homozygous animals that lack the muscle protein dystrophin, have high serum levels of muscle enzymes, and possess histological lesions similar to human muscular dystrophy. The histological features, linkage, and map position of mdx make these mice a worthy animal model of Duchenne muscular dystrophy. Mdx mice have a progressive muscle degeneration starting about three weeks of age. At eight weeks, the mdx forelimb strength decreases while the hind limbs show normal strength. These findings reflect the progression of the acute phase of muscle necrosis in the young mdx mice (Grounds et al., 2008). Muscle atrophy, inflammation and fibrosis are present in the mdx mice at eight weeks of age (Consalvi S. et al. Histone Deacetylase Inhibitors in the Treatment of Muscular Dystrophies: Epigenetic Drugs for Genetic Diseases. (2011) Mol. Med. 17:457-465).

Experiment Description:

2 months old mdx mice were randomized in three groups of ten animals each.

Control group (CTR) was treated with a solution of methylcellulose (0.5%, gavage) once a day for 90 days.

Test group (ITF) was treated with a diethyl-[6-(4-hydroxycarbamoyl-phenyl-carbamoyloxy-methyl)-naphthalen-2-yl-methyl]-ammonium chloride (ITF2357) solution (10 mg/Kg, gavage) once a day for 90 days.

Trichostatin A group (TSA) was treated with a TSA solution (0.6 mg/Kg, i.p.) once a day for 90 days.

Example 1

Givinostat Increases Resistance to Fatigue in Mdx Mice after 90 Days Treatment (Treadmill Test)

The effect of the treatments was investigated on exercise performance in vivo by the treadmill test, according to the following protocol:

Run: 8 cm/sec for 5 min
After 5 min—progressive increase of 2 cm/min
Numb: 0.2 mA (stable)
End of run if stop more than 5-10 sec on plate.

As shown in FIG. 1, ITF treated group had a longer time to exhaustion than the CTR group.

Example 2

Givinostat Treatment Increases the Size of Muscles in Mdx Mice (Macroscopic Evaluation)

At the end of the experiment described above, the mice were sacrificed for skeletal muscle analysis by macroscopic evaluation.

Figure 2:
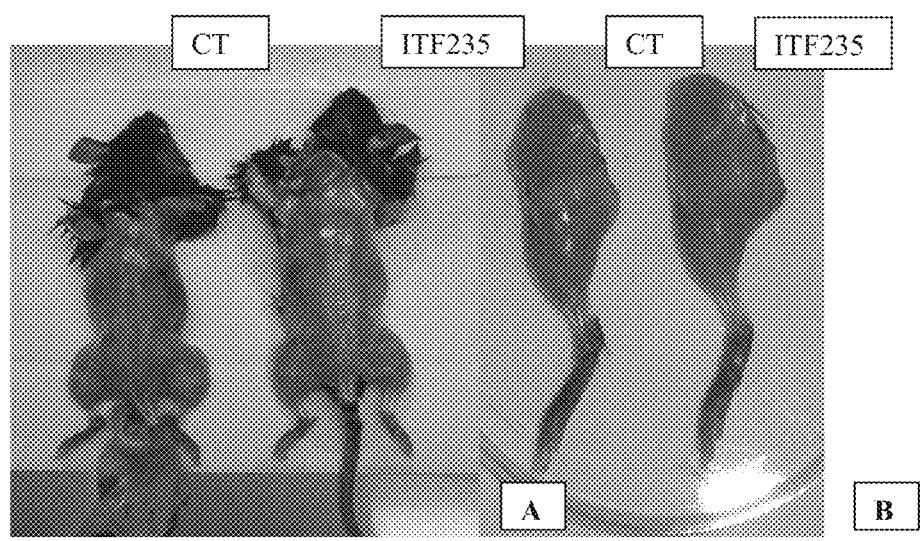
FIG. 2 shows that ITF treated group had an increased muscle size compared to the CTR group: (A) whole naked bodies, and (B) hind limb legs isolated from mdx.

As shown in FIG. 2, A) (whole naked bodies) and B) (hind limb legs isolated from mdx), ITF treated group had an increased muscle size compared to the CTR group.

Example 3

Givinostat Reduces the Fibrosis Area in Treated Mdx Mice (Masson's Trichrome Staining)

Figure 3:
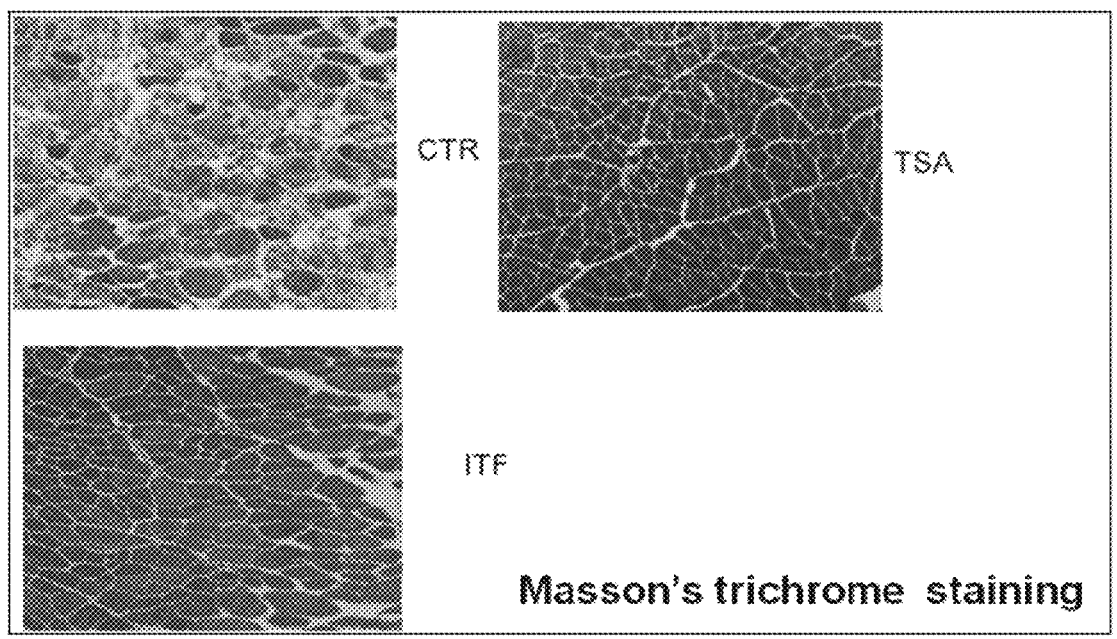
FIG. 3 shows the analysis of "tibialis anterior" (TA) section area by Masson's trichrome staining in control group, TSA-treated group, and ITF-treated group.

At the end of the treatment period, analysis of "tibialis anterior" (TA) section area by Masson's trichrome staining, revealed a strong reduction of fibrotic (blue) area for ITF treated group as shown in FIG. 3.

What is claimed is:

1. A method for treating muscular dystrophy in a patient, comprising administering to a patient in need thereof active ingredients consisting of (i) diethyl-[6-(4-hydroxycarbamoyl-phenylcarbamoyloxymethyl)-naphthalen-2-yl-methyl]-ammonium chloride, or the pharmaceutically acceptable salts and/or solvates thereof, and (ii) one additional anti-inflammatory agent.

2. The method according to claim 1, wherein said additional anti-inflammatory agent is a steroid.

3. The method according to claim 2, wherein said steroid is selected from the group consisting of prednisolone, prednisone, deflazacort, hydrocortisone, methylprednisolone, dexamethasone, betamethasone, triamcinolone, beclometasone, fludrocortisone acetate, and deoxycorticosterone acetate.

4. The method according to claim 1, wherein said diethyl-[6-(4-hydroxycarbamoyl-phenylcarbamoyloxymethyl)-naphthalen-2-yl-methyl]-ammonium chloride, or the pharmaceutically acceptable salts and/or solvates thereof, and said additional anti-inflammatory agent are administered simultaneously, separately, or sequentially.

5. The method according to claim 1, wherein said muscular dystrophy is Duchenne muscular dystrophy.

6. The method according to claim 1, wherein the administration to the patient is on a daily basis.

7. The method according to claim 1, wherein said diethyl-[6-(4-hydroxycarbamoyl-phenylcarbamoyloxymethyl)-naphthalen-2-yl-methyl]-ammonium chloride, or the pharmaceutically acceptable salts and/or solvates thereof is administered in an amount ranging from 0.5 to 15 mg/kg/day.

8. The method according to claim 1, wherein said patient is a child.

9. The method according to claim 8, wherein said diethyl-[6-(4-hydroxycarbamoyl-phenylcarbamoyloxymethyl)-naphthalen-2-yl-methyl]-ammonium chloride, or the pharmaceutically acceptable salts and/or solvates thereof is administered in an amount ranging from 1 to 10 mg/kg/day.

10. The method according to claim 1, wherein said diethyl-[6-(4-hydroxycarbamoyl-phenylcarbamoyloxymethyl)-naphthalen-2-yl-methyl]-ammonium chloride, or the pharmaceutically acceptable salts and/or solvates thereof is administered in the form of a pharmaceutical composition comprising the same together with at least one physiologically acceptable excipient.

11. The method according to claim 10, wherein said pharmaceutical composition is administered by oral, sublingual, rectal, intravascular, intravenous, or subcutaneous route.

12. The method according to claim 11, wherein said pharmaceutical composition is in a solid or a liquid form.

13. The method according to claim 12, wherein said solid form is selected from the group consisting of powder, tablet, granulate, aggregate, compressed pill, coated pill, hard gelatin capsule, and gelatin capsule.

14. The method according to claim 12, wherein said liquid form is a suspension or a syrup.

15. The method according to claim 1, wherein said diethyl-[6-(4-hydroxycarbamoyl-phenylcarbamoyloxymethyl)-naphthalen-2-yl-methyl]-ammonium chloride is in a monohydrate form.

16. The method according to claim 1, wherein said diethyl-[6-(4-hydroxycarbamoyl-phenylcarbamoyloxymethyl)-naphthalen-2-yl-methyl]-ammonium chloride is in a crystal form.

\* \* \* \* \*